(12) United States Patent
Maniga

(10) Patent No.: US 9,271,917 B2
(45) Date of Patent: Mar. 1, 2016

(54) METHOD AND APPARATUS FOR DELIVERY OF A MEASURED DOSAGE OF A NON-AEROSOL, NON-SPRAY FOAM COMPOSITION OF MINOXIDIL

(71) Applicant: Nyangenya Maniga, Gilbert, AZ (US)

(72) Inventor: Nyangenya Maniga, Gilbert, AZ (US)

( * ) Notice: Subject to any disclaimer, the term of this patent is extended or adjusted under 35 U.S.C. 154(b) by 0 days.

(21) Appl. No.: 14/588,108

(22) Filed: Dec. 31, 2014

(65) Prior Publication Data

US 2015/0111913 A1     Apr. 23, 2015

Related U.S. Application Data

(63) Continuation-in-part of application No. 13/019,181, filed on Feb. 1, 2011, now abandoned, which is a continuation-in-part of application No. 13/016,583, filed on Jan. 28, 2011.

(60) Provisional application No. 61/299,572, filed on Jan. 29, 2010.

(51) Int. Cl.
| | | |
|---|---|---|
| *A61K 8/49* | (2006.01) | |
| *A61K 8/60* | (2006.01) | |
| *A61Q 7/00* | (2006.01) | |
| *A61K 8/04* | (2006.01) | |
| *B05B 11/00* | (2006.01) | |
| *A01N 43/54* | (2006.01) | |
| *A61K 8/365* | (2006.01) | |

(52) U.S. Cl.
CPC ............. *A61K 8/4953* (2013.01); *A01N 43/54* (2013.01); *A61K 8/046* (2013.01); *A61K 8/365* (2013.01); *A61K 8/4926* (2013.01); *A61K 8/604* (2013.01); *A61K 8/608* (2013.01); *A61Q 7/00* (2013.01); *B05B 11/3087* (2013.01)

(58) Field of Classification Search
CPC ..... A61K 8/046; A61K 8/4953; A61K 8/608; A61K 8/00; A61Q 7/00; B05B 11/3087
See application file for complete search history.

(56) References Cited

U.S. PATENT DOCUMENTS

| | | |
|---|---|---|
| 4,596,812 A | 6/1986 | Chidsey |
| 4,820,512 A | 4/1989 | Grollier |
| 4,828,837 A | 5/1989 | Uster |
| 5,030,442 A | 7/1991 | Uster |
| 5,225,189 A | 7/1993 | Pena |
| 5,620,980 A | 4/1997 | Samour |
| 5,834,014 A | 11/1998 | Weiner |
| 6,465,514 B1 | 10/2002 | Hallam |
| 6,596,266 B2 | 7/2003 | Catalfo |
| 6,946,120 B2 | 9/2005 | Wai-Chiu So |
| 7,442,369 B1 | 10/2008 | Pena |
| 7,749,489 B2 | 7/2010 | Malek |
| 7,803,357 B2 | 9/2010 | Cappello |
| 2005/0079139 A1 | 4/2005 | Jacques |
| 2008/0206156 A1 | 8/2008 | Cronk |

*Primary Examiner* — Timothy Thomas
*Assistant Examiner* — Andrew S Rosenthal
(74) *Attorney, Agent, or Firm* — Kevin Hazen

(57) ABSTRACT

A non-pressurized container that contains one or more of: a foamable composition of minoxidil, or a pharmaceutically acceptable salt thereof, and a dihydrotestosterone blocker in a formulation with a precise density and viscosity to yield a foam with a temperature sensitivity and shear strength designed for inverted application and immediate targeted release at body temperature under a minimal hand applied pressure to the scalp.

9 Claims, 5 Drawing Sheets

METHOD AND APPARATUS FOR DELIVERY OF A MEASURED DOSAGE OF A NON-AEROSOL, NON-SPRAY FOAM COMPOSITION OF MINOXIDIL

CROSS-REFERENCES TO RELATED APPLICATION

This application is a continuation-in-part of U.S. patent application Ser. No. 13/019,181 filed Feb. 1, 2011, which is a continuation-in-part of U.S. patent application Ser. No. 13/016,583 filed Jan. 28, 2011, which claims the benefit of U.S. provisional patent application No. 61/299,572 filed Jan. 29, 2010, all of which are incorporated herein in their entirety by this reference thereto.

BACKGROUND OF THE INVENTION

1. Field of the Invention

The present invention relates to a non-aerosol, non-spray delivery apparatus and method of use thereof for delivery of a minoxidil composition or a salt thereof for the treatment and prevention of androgenic alopecia, male and female pattern baldness.

2. Description of Related Art

Minoxidil (chemical formula 2,4-diamino-6-piperidinylpyrimidine-3-oxide) is the active ingredient of Rogaine® (New Brunswick, N.J.), which is approved by the U.S. Food and Drug Administration as a safe and effective drug. It is marketed by Pfizer for the treatment and prevention of androgenic alopecia.

Numerous investigators have demonstrated that minoxidil can stimulate visible hair growth in a majority of balding subjects. The structure and use of this compound is described in U.S. Pat. No. 4,139,619 and U.S. Pat. No. 4,596,812. Minoxidil has varying degrees of efficacy for moderating androgenic alopecia, depending on the degree of baldness, its duration, the age of the patient, and on the concentration of the drug in an appropriate delivery vehicle.

There are many challenges in the topical application of pharmaceutically active agents. One major objective is to achieve percutaneous penetration of the active agent to the site of treatment. It is also desirable for the composition to have desirable cosmetic characteristics, for easy and smooth application, and for administration without a noticeable residue on the surface of the skin. It is further desirable that the composition not cause irritation or discomfort. It is still further desirable that application is convenient in terms of time requirements and in terms of necessary clean-up after application.

Topical solutions have not been satisfactory for use in treating the scalp as they tend not to remain in place long enough for satisfactory amounts of the drug to be absorbed. The solution readily runs off the site of application and therefore, it is difficult to apply controlled amounts using the minoxidil in solution form.

Formulations of minoxidil, such as jellies and ointments, have been proposed. These compositions are not pharmaceutically elegant and also are not suitable for use as treatments for stimulating the growth of hair from a cosmetic point of view. Lotion and gel topical dosage forms have the disadvantage of extended rub-in and leave oily residues.

Commercially available Rogaine®, disclosed in U.S. Pat. No. 6,946,120 includes an aerosol foam, which is filled into a pressurized container together with a propellant fluid. The composition is foamed prior to the application by means of a propellant fluid.

Aerosol containers are in widespread use as liquid dispensing devices. However, aerosol containers require the use of a pressure container and a propellant fluid to create foam. Propellants provide the appropriate vapor pressure within aerosol containers for the expulsion of the formulation as a spray or semisolid when the valve is opened. Typical propellants include liquefied petroleum gases; such as mixture of propane, isobutene, and n-butane; chlorofluorocarbons; methyl ethyl ether; and dimethyl ether, which are flammable, harmful and toxic volatile organic compounds. Further, it is known that the propellant fluid frequently constitutes a source of environmental pollution and sometimes the aerosol container represents a hazard when disposed of since the propellant material are explosive or flammable. Generally, chlorofluorocarbons are banned from use due to their ozone depletion effect, liquefied petroleum gases are flammable, and other propellants such as nitrous oxide may have physiological effects.

Still further, aerosol containers can not be completely emptied or refilled, increasing waste. Aerosol containers are discarded once the supply of liquid dispersant is exhausted or when the supply of propellant material has been used to the extent that there is no longer sufficient pressure within the container to discharge the liquid as intended. Further, pressure containers can only be cylindrical, drastically limiting the choice of container shape. An additional disadvantage is that pressure containers are more expensive than non-pressurized containers and have higher manufacturing costs.

Patents related to the current invention are summarized here.

Aerosol Foam

T. Wai-Chiu So, et. al., "Pharmaceutical Composition", U.S. Pat. No. 6,946,120 B2 (Sep. 20, 2005) describe a pharmaceutical composition for topical administration including at least five percent by weight of a piperidinopyrimidine derivative or an acceptable salt thereof, an acid, a solvent composition including water, a lower alcohol and co-solvents consisting of aromatic and polyhydric alcohols, where the co-solvent includes less than approximately ten percent by weight of propylene glycol.

Foam Spray

E. Jacques, et. al., "Minoxidil Pharmaceutical Foam Formulation", U.S. patent application no. 2005/0079139 A1 (Apr. 14, 2005) describe a pharmaceutical foam formulation in a dosage form including at least one active ingredient selected from the group consisting of minoxidil, minoxidil sulfate, other soluble minoxidil salts, a surfactant, and water; the formulation being adapted to form a foam when administered by spraying.

Aerosol Liquid Spray

P. Cronk, et. al., "Continuous Spray Scalp Therapy and Dispensing Systems for Same", U.S. patent application no. 2008/0206156 A1 (Aug. 28, 2008) describes continuous spray medications, spray medication dispensing systems, and methods for treating alopecia, in which a continuous mist of a scalp medication, such as minoxidil, finesteride, copper peptides, DHT inhibitors and/or androgen receptor blockers, disposed within a pharmacologically acceptable carrier solution, is administered in an amount sufficient to stimulate or maintain hair growth.

P. Uster, et. al., "Non-crystalline Minoxidil Composition", U.S. Pat. No. 5,030,442 (Jul. 9, 1991) describe an aqueous, non-crystalline minoxidil composition for topical use containing minoxidil complexed with an amphipathic compound, oleic acid, and acceptable excipients, which has improved flux through human cadaver skin and is formulated in an aqueous vehicle or dispersed in fluorochlorocarbon solvent for spray delivery.

P. Uster, et. al., "Non-crystalline Minoxidil Composition, its Production and Application", U.S. Pat. No. 4,828,837 (May 9, 1989) describe an aqueous, non-crystalline minoxidil composition for topical use containing minoxidil complexed with an amphipathic compound containing a single lipophilic chain moiety and a sulfate, sulfonate, phosphate and phosphonate polar moiety, and having a pK less than five. the composition is formulated in ointment form, in an aqueous vehicle, or dispersed in a fluorochlorocarbon solvent for spray delivery.

Aqueous Vehicle

J. Cappello, "Topical and Transdermal Treatments Using Urea Formulation", U.S. Pat. No. 7,803,357 B2 (Sep. 28, 2010) describes a topical application of a composition of urea and a chemotherapeutic agent such as sclerosing agents, vasodilators, botulinum toxin, and minoxidil that is effective in treating spider veins, erectile dysfunction, facial wrinkles, hair loss, and baldness.

S. Malek, "Topical Administration Carrier Composition and Therapeutic Formulations Comprising Same", U.S. Pat. No. 7,749,489 B2 (Jul. 6, 2010) describes a topically administered carrier composition including water, glycerin, and polysorbate, which retards the evaporative losses of the solvent component and systemic migration losses of the active ingredient to provide sustained topical action for use in formulations containing active ingredients, such as minoxidil.

K. Hallam, et. al., "Methods and Compositions for the Promotion of Hair Growth", U.S. Pat. No. 6,465,514 B1 (Oct. 15, 2002) describe compositions, medicaments, and methods for the promotion of hair growth, topically applied to the scalp by use of an eyedropper or other suitable means, including either local anesthetics of the secondary and tertiary amino type and/or niacin. The compositions and medicaments include minoxidil and either procaine hydrochloride or niacin or procaine hydrochloride and niacin in a non-sulfur-containing carrier.

C. Chidsey, III, et. al., "Methods and Solutions for Treating Male Pattern Alopecia", U.S. Pat. No. 4,596,812 (Jun. 24, 1986) describe a method for treating male pattern baldness, which includes regular topical application to the human scalp of a composition containing 6-amino-1,2-dihydro-1-hydroxy-2-imino-4-piperidinopyrimidine as one of its active ingredients.

Gel/Ointment/Cream

L. Pena, et. al., "Compositions of Minoxidil", U.S. Pat. No. 7,442,369 B1 (Oct. 28, 2008) describe novel compositions comprising minoxidil, a thickening agent, and a pharmaceutically acceptable solvent; a process for making a gel composition including minoxidil; and methods for using the compositions for treating and preventing hair loss in a patient.

C. Samour, "Method for Treating Hair Loss", U.S. Pat. No. 5,620,980 (Apr. 15, 1997) describes the combination of minoxidil and 2-n-nonyl-1,3-dioxolane for promoting hair growth when applied once daily.

L. Pena, "Minoxidil Gel", U.S. Pat. No. 5,225,189 (Jul. 6, 1993) describes a pharmaceutical gel containing minoxidil for topical application.

J. Grollier, "Composition in the Form of a Gel for Inducing and Stimulating Hair Growth and for Decreasing Their Loss, Based on Piperidinopyrimidine Derivatives", U.S. Pat. No. 4,820,512 (Apr. 11, 1989) describes a gel composition for inducing and stimulating hair growth and for reducing hair loss based on piperidinopyrimidine derivatives.

Oral in Conjunction with Topical Application

C. Catalfo, et. al., "Compositions Containing Minoxidil and Saw *Palmetto* for Treating Baldness", U.S. Pat. No. 6,596,266 B2 (Jul. 22, 2003) describe compositions containing minoxidil as an active ingredient, other active agents and/or enhancer agents, such as saw *palmetto* extract and nettle root extract, and methods of using the compositions to treat male patterned baldness and to stimulate hair growth on the scalp.

Encapsulation

N. Weiner, et. al., "Stimulation of Hair Follicles", U.S. Pat. No. 5,834,014 (Nov. 10, 1998) describe a novel method and delivery system for the topical delivery of a therapeutic weak acid or a base material, such as minoxidil, that utilizes a therapeutic material, which is modified to make it more hydrophilic, encapsulated in a lipid vesicle, preferably a non-phospholipid vesicle.

Problem

There remains in the art a need for an effective formulation and/or delivery method for delivery of minoxidil and/or a minoxidil salt.

SUMMARY OF THE INVENTION

The invention comprises a non-aerosol, non-spray delivery apparatus and method of use thereof for delivery of a minoxidil composition or a salt thereof.

BRIEF DESCRIPTION OF THE DRAWINGS

A more complete understanding of the present invention is derived by referring to the detailed description and claims when considered in connection with the Figures, wherein like reference numbers refer to similar items throughout the Figures.

DETAILED DESCRIPTION OF THE INVENTION

Figure 1:
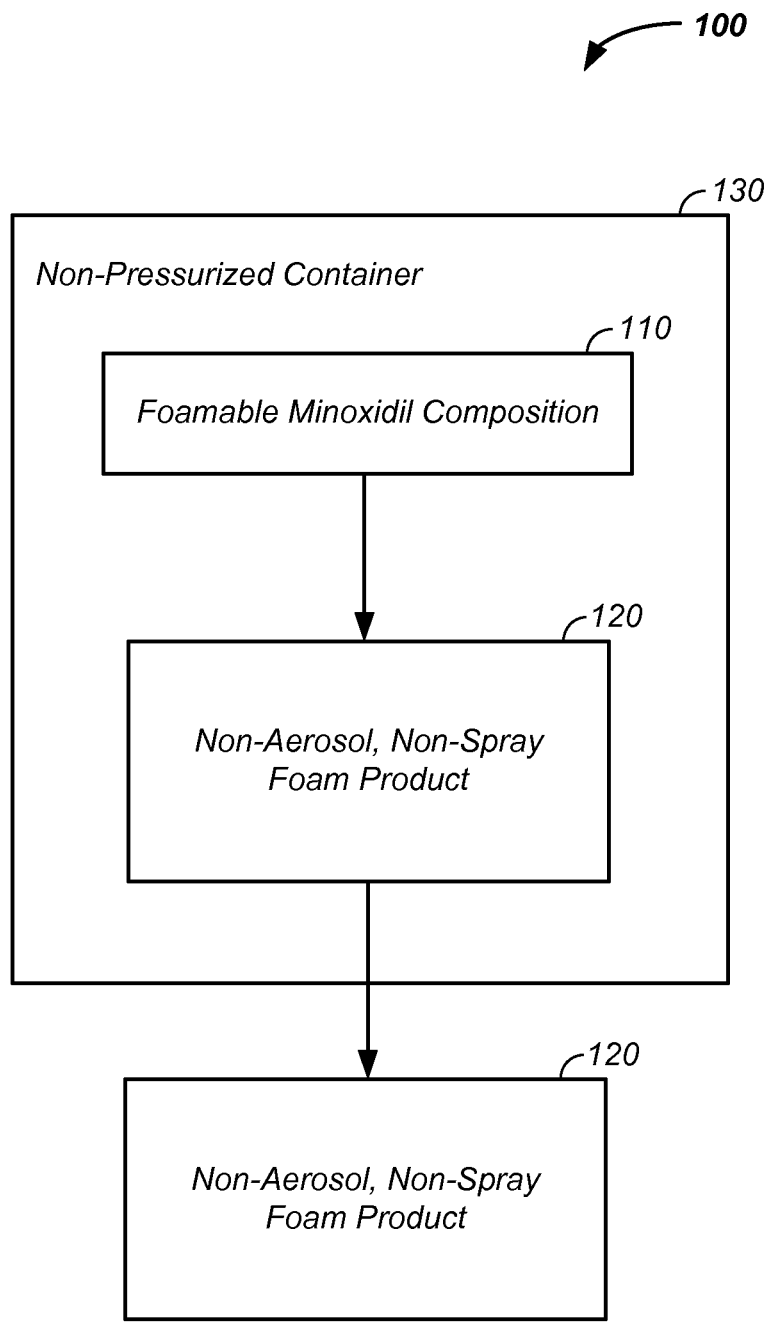
FIG. 1 illustrates key features of a foamable non-aerosol, non-spray product composition and delivery system.

The invention comprises a non-pressurized container apparatus and method of use thereof for delivery of an active ingredient, such as: (1) minoxidil or a pharmaceutically acceptable salt thereof and/or (2) a Dihydrotestosterone (DHT) blocker for the treatment and prevention of androgenic alopecia as a temperature sensitive, density and viscosity controlled, non-aerosol, non-spray foam product.

In one embodiment, a non-pressurized container contains one or more of: an active ingredient, such as: (1) minoxidil or a pharmaceutically acceptable salt thereof a foamable composition of minoxidil, or a pharmaceutically acceptable salt thereof and/or (2) a dihydrotestosterone (DHT) blocker, such as: cetearyl glucoside and/or 8-hydroxy quinolone sulfate; an aqueous-alcoholic solvent medium which enables the active ingredient(s) to be solubilized, a surfactant, such as oleth-20, a foam stabilizer, such as lauryl glucoside, a sunscreen, biotin, and/or lactic acid.

In another composition, the active ingredients are optionally delivered in a measured dosage as a temperature sensitive foam using a non-pressurized container, where the foam is produced within the container without use of a propellant. For example, the foamable non-aerosol, non-spray composition containing minoxidil, a salt thereof as the pharmaceutically active compound, and/or a DHT blocker is dispensed in a measured dosage as a liquid foam to the human scalp. The delivery of the foam at room temperature allows delivery of the active ingredient of minoxidil without dispensing a runny liquid, which runs off of the hands or scalp resulting in non-uniform coverage and an unknown delivery mass of the active ingredient. The delivery of the room temperature foam to the scalp allows natural convection and/or thermal transfer of heat from the head to breakdown the foam allowing targeted delivery of the active agents to the hair and/or scalp.

In another embodiment, a foamable composition includes: approximately one-half percent or greater minoxidil, or a pharmaceutically acceptable salt thereof, by weight, based on total weight of the foamable composition; a solvent system, the solvent system comprising an aqueous-alcoholic solvent medium which enables the minoxidil or the pharmaceutically acceptable salt thereof to be solubilized; a surfactant, the surfactant comprising oleth-20; and a foam stabilizer, the foam stabilizer comprising lauryl glucoside.

In still another embodiment, a foamable composition includes: approximately ½, 1, 2, 3, 4, or 5 percent or more minoxidil, or a pharmaceutically acceptable salt thereof, by weight, based on total weight of the foamable composition; A DHT blocker, cetearyl glucoside, 8-hydroxyquiniline sulfate, biotin, lactic acid, an alcohol, a solvent system, the solvent system comprising an aqueous-alcoholic solvent medium which enables the minoxidil or the pharmaceutically acceptable salt thereof to be solubilized, and/or a surfactant, the surfactant comprising oleth-20; and a foam stabilizer, the foam stabilizer comprising lauryl glucoside.

Hereinafter, for clarity minoxidil, cetearyl glucoside, and/or 8-hydroxyquinoline sulfate optionally refers to the active ingredient or vise-versa. However, all formulations and all delivery methods described herein additionally apply to delivery of a pharmaceutically acceptable salt of minoxidil as the active ingredient and/or to the delivery of a DHT blocker/inhibitor.

Advantages

Delivery of a measured dosage of a foam product directly to the human scalp from the container has a number of advantages, including:
  easy and smooth delivery of the product directly to the scalp;
  delivery of a measured dosage of the formulation comprising minoxidil or a salt thereof;
  economic delivery of the formulation; and
  delivery from a non cylindrical container.

The foam is non-runny, easy to apply, breaks easily with shear, and uses a low residue delivery vehicle. When the foam is applied, body heat causes the foam structure to break down and deposit the active ingredient in the form of a vehicle resembling a solution. The foam composition is light, gentle, and easy to control on application to the desired area of the scalp. The foam allows controlled and precise delivery of a dosage of the active ingredient to the scalp without an intermediate transfer container, a hand, and/or the running of the active agent off of the scalp in a liquid deliver vehicle.

Foamable Liquid Composition

In a first embodiment, the foamable liquid composition optionally includes:
  minoxidil or a pharmaceutically acceptable salt thereof as the active ingredient;
  a solvent system;
  a surfactant; and
  a stabilizer.

Each of the minoxidil, the solvent system, the surfactant, and the stabilizer are further described, infra.

In a second embodiment, the foamable liquid composition optionally includes:
  minoxidil or a pharmaceutically acceptable salt thereof as the active ingredient;
  a DHT blocker;
  cetearyl glucoside;
  8-hydroxyquinoline sulfate;
  biotin;
  lactic acid;
  a thinning agent;
  an alcohol; and/or
  ether.

Each of the formulation constituents are further described, infra.

Referring now to FIG. 1, a foam delivery method 100 of a non-aerosol, non-spray foam product 120 includes: a foamable minoxidil composition 110 or a foamable liquid composition held in a non-pressurized container 130 and a method of creating the non-aerosol, non-spray foam product 120 within the container 130 and dispensing the non-aerosol, non-spray foam product 120 from the container 130.

Figure 2:
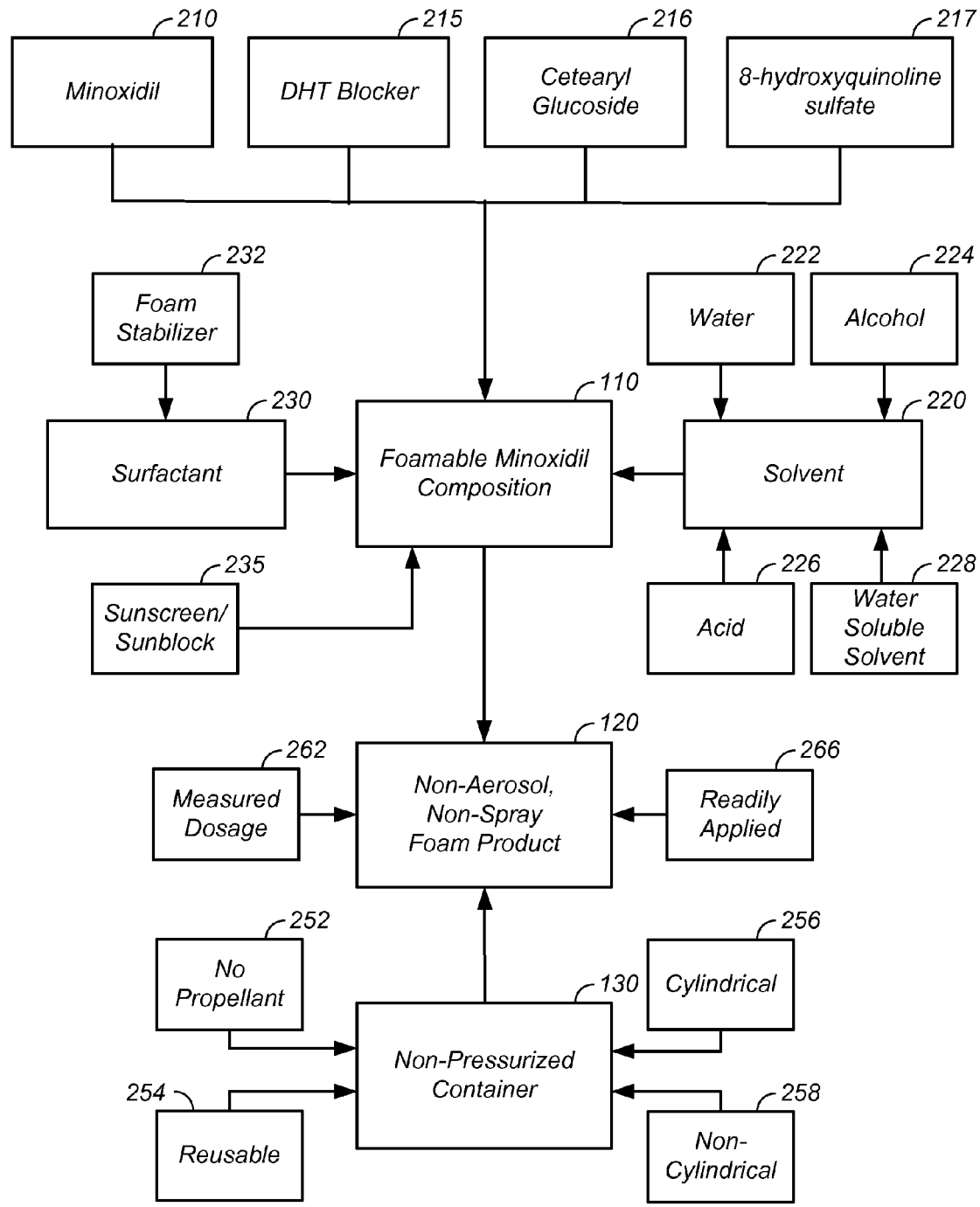
FIG. 2 illustrates formulation of the foamable non-aerosol, non-spray product.

Referring now to FIG. 2, details of use of the non-pressurized container 130 to dispense the foamable liquid composition and the active ingredient(s) as the non-aerosol, non-spray foam product 120 for the treatment and prevention of hair loss in humans are provided. The foamable minoxidil composition is preferably dispensed using non-aerosol, non-spray means as the formulations taught herein that specify density and viscosity are suitable for foam formation and longevity with a low pressure not aerosol system, as the aerosol shear strength will overcome surface forces inherent to foam stability of the preferred formulations described herein.

Foamable Liquid Formulation

Still referring to FIG. 2, details of the foamable minoxidil composition 110 are provided. The foamable minoxidil composition 110 optionally includes one or more of:
  a DHT blocker 215;
  cetearyl glucoside 216;
  8-hydroxyquinoline sulfate 217;
  a surfactant 230, where the surfactant optionally includes:
    a foam stabilizer 232;
  a solvent 220, such as
    water 222;
    an alcohol 224;
    an acid 226; and
    a water soluble solvent 228; and
  a sunscreen and/or a sun block 235.

Minoxidil

Minoxidil 210 or a pharmaceutically acceptable salt thereof is preferably used in portions of between one-half and ten percent by weight and preferably in portions of between two and five percent by weight relative to the total weight of the composition. The inventor has surprisingly determined that while competing methods of delivery of minoxidil require five percent or more of minoxidil, the foamable composition delivery method, established density and viscosity, and temperature sensitivity combine to deliver a targeted dosage of minoxidil allowing smaller concentrations of minoxidil to be pharmaceutically effective, such as less than 1, 2, 3, or 4 percent minoxidil by weight.

DHT

A major cause of hair loss is dihydrotestosterone (DHT), a hormone synthesized from male testosterone, causes hair follicle miniaturization, which leads to male pattern baldness. A DHT blocker inhibits DHT and thus stops/reduces hair loss. DHT blockers that are optionally included in the formulation described herein in combination with minoxidil include: saw *palmetto*; a concentrated root extract of nettle; an extract of *Prunus* African, such as pygeum; green tea; emu oil, pumpkin seed oil; soy isoflavones; and/or zinc. Preferred DHT blockers are cetearyl glucoside do to its surfactant and emulsifier properties; biotin; and 8-hydroxyquinoline sulfate. Advantages of green tea and emu oil are their additional ability to aid hair regrowth.

Solvent

The foamable minoxidil composition is preferably in a solvent 220. Preferably the solvent 220 is an aqueous-alcoholic medium, which enables solubilization of the minoxidil 210. In a first example, the solvent 220 includes water 222 from twenty to eighty percent by weight. Preferably the water 222 makes up thirty to sixty percent of the foamable minoxidil composition 110 by weight.

In an first example, the solvent 220 includes an acid 226 at a concentration of one-half to five percent by weight of the foamable minoxidil composition 110. The acid 226 is optionally any inorganic acid, any organic acid with chain length of eight carbons or less, or a molecule containing eight carbons or less. A preferred composition of the solvent 220 includes:
  lactic acid in proportions between about one and four percent by weight;
  a lower alcohol 224 with one to four carbon atoms, such as methanol, ethanol, propanol and isopropyl alcohol, preferably ethanol in proportions of between about one-tenth and fifty percent by weight and more preferably between about five and thirty percent by weight; and
  one or more water soluble solvents 228, such as butylene glycol, glycerin, polyglycerin, ethylene glycol, and propylene glycol, preferably propylene glycol in proportions of between about zero and twenty percent by weight, and more preferably between about five and fifteen percent by weight,
where all of the weights are relative to the total weight of the foamable minoxidil composition 110.

Surfactant

Foam is produced by the introduction of air or other gas into a liquid phase, during which time the bubbles become encapsulated in a film of the liquid. The thin liquid film separating two or more gas bubbles is referred to as a lamellar film.

For a liquid to form foam, it must be able to form a membrane around the gas bubbles possessing a form of elasticity that opposes the thinning of the lamellae as a result of loss or drainage of the liquid. Foaming does not occur in pure liquids because no such mechanism for the retardation of lamellae drainage or interfacial stabilization exists. However, when surface-active substances, such as a surfactant, is present their adsorption at the gas-liquid interface serves to retard the loss of liquid from the lamellae and in some instances, to produce a more mechanically stable system.

The formation and persistence of foams under various conditions is explained by the complimentary effects known as the Gibbs-Marangoni effects. The Gibbs effect states that the surface tension of a solution will decrease as the concentration of the surfactant in solution increases until the critical micelle concentration (cmc) is achieved. The Marangoni effect states that there is a finite, diffusion rate based, time during which the surface-active molecules in the bulk solution diffuse to the interface to lower the surface tension of a newly formed surface.

Therefore, the ability of a surfactant to perform as a foaming agent is dependent primarily on its effectiveness at reducing the surface tension of the solution, the rate of diffusion of the surfactant molecules in the bulk solution to the interface to reduce the surface tension, the rate of adsorption of the surfactant molecules at the interface, its properties with regard to surface pressures or disjoining pressures due to overlapping of the surface layers in thin films, and the elastic properties it imparts to interfaces.

Hence, the effectiveness of a surfactant is determined by how the surfactant interacts with the other constituents of the system in question. However, the Gibbs-Marangoni effects are not sufficiently detailed to allow prediction of foam formation and foam failure as a function of temperature differences of 10-20° C., especially over a narrow time period of less than 1, 5, 10, 20, 60, 120, or 180 seconds. Hence, a custom-built surfactant formulation is herein presented to achieve a combination of surfactant actions to suit the individual needs of the system.

A preferred embodiment of the liquid foam according to the invention contains at least one surfactant 230. The surfactant 230 is preferably contained in an amount of one-tenth to five percent by weight of the foamable minoxidil composition 110, and more preferably is in the range of about two-tenths to one percent by weight of the foamable minoxidil composition 110. Suitable surfactants have emulsifying, solvating, and foam-forming or foam-stabilizing properties; are preferably nonionic; and have a hydrophilic-lipophilic balance (HLB) value of greater than about fifteen. In particular, the surfactant oleth-20 is preferred in proportions between about one tenth and five percent by weight of the foamable minoxidil composition 110 and more preferably between about two-tenths and one percent by weight relative to the total weight of the foamable minoxidil composition 110.

Other surfactants optionally used with the present formulation include, but are not limited to: any combination of anionic, cationic, non-ionic, zwitterionic, or amphoteric surfactants and non-ionic block copolymers with an HLB value of greater than fifteen.

Stabilizer

Optionally, the non-aerosol, non-spray foam product 120 is maintained with a foam stabilizer 232. In the application of treatment of the human scalp for androgenic alopecia, male or female pattern baldness, the maintenance of foam is important to allow a known and suitable period of contact of the minoxidil 210 to the scalp.

Lamellar films between adjacent bubbles can be easily stretched as a result of gravity, agitation, drainage, and other motion leading to collapsing of the foam. In spite of their tendency to collapse, however, foams can be prepared that have a lifetime or persistence of minutes, days, or even months. Low persistence foams remain for a very short time and collapse due to overwhelming effects of surface tension and gravitational forces. More persistence foams can be produced by introduction of small amounts of amphiphilic substances or a foam stabilizer 232 to the aqueous system.

The foam stabilizer 232 alters the characteristics of the aqueous system and hence enhances the stability of the foam and extends the lifetimes as a result of one or several of the following: (1) increasing the viscosity in the liquid phase, slowing drainage of the liquid from between the bubble interfaces, as well as providing a cushion effect to absorb shocks resulting from random or induced mechanical disturbances/motion; (2) increasing the surface viscosity, which also retards liquid loss from between interfaces by a viscous drag type of mechanism; (3) enhancing surface effects such as the Gibbs and Marangoni effects, which act to "heal" areas of film thinning due to loss or drainage of liquid; and (4) electrostatic and steric repulsion between adjacent interfaces due to the adsorption of ionic and nonionic surfactants, polymers, or other compounds. The foam stabilizer 232 also has the effect of lowering the surface tension of the system, which reduces the work required for the initial formation of the foam.

A preferred embodiment of the foamable minoxidil composition 110 contains at least one stabilizer 232. The stabilizer 232 is preferably contained in an amount of about 0.05 to 0.5 percent, and more preferably from one tenth to five tenths percent by weight. In particular, the stabilizer includes lauryl glucoside with a portion between about 0.05 and 0.5% by weight and more preferably between one-tenth and five-tenths percent by weight relative to the total weight of the composition.

Other optional foam stabilizers 232 used with the present formulation include, but are not limited to: any fatty amine oxide, a quaternary amine, or a cellulose derivatives, such as methyl cellulose and ethyl cellulose.

It is a principal object to provide the liquid foamable minoxidil composition 110 or formulation for topical administration to the scalp where:
the active ingredient comprises minoxidil 210 or a pharmaceutically acceptable salt thereof, preferably between about one-half and ten percent by weight and more preferably between about two and five percent by weight relative to the total weight of the foamable minoxidil composition 110;
the solvent 220 or aqueous medium, which enables the minoxidil to be solubilized, preferably includes:
water 222 from about twenty to eighty percent by weight and more preferably from about thirty to sixty percent relative to the total weight of the foamable minoxidil composition 110;
acid 226 from about one-half to five percent by weight, such as any inorganic acid or any organic acid with eight carbons or less, preferably lactic acid between about one and four percent by weight of the foamable minoxidil composition 110;
a lower alcohol with one to four carbon atoms, such as methanol, ethanol, propanol, and isopropyl alcohol, preferably ethanol in proportions of between about one-tenth and fifty percent by weight and more preferably between about five and thirty percent by weight of the foamable minoxidil composition 110; and
a water soluble solvent 228, such as butylene glycol, glycerin, polyglycerin, ethylene glycol, and propylene glycol, preferably propylene glycol in proportions of between about zero and twenty percent by weight and more preferably between about five and fifteen percent by weight; and
at least one surfactant 230, such as any combination of anionic, cationic, non-ionic, zwitterionic surfactant, and non-ionic block copolymers with an HLB value of greater than about fifteen, preferably oleth-20 in proportions of about one-tenth to five percent by weight and more preferably from about two-tenths to one percent by weight of the foamable minoxidil composition 110, and
at least one foam stabilizer 232, such as any fatty amine oxides, quaternary amines, or cellulose derivatives, such as methyl cellulose and ethyl cellulose, but preferably lauryl glucoside in proportions of about 0.05 to 0.5 percent by weight and more preferably from about one-tenth to one-half percent by weight of the foamable minoxidil composition 110.

Method of Dispensing Non-Aerosol, Non-Spray Foam

Another object relates to the dispensing of stable non-aerosol, non-spray foam that breaks easily with shear as the vehicle system for dispensing out the liquid formulation comprising the active ingredient minoxidil or a pharmaceutically acceptable salt thereof.

Aerosol Foam

Figure 3:
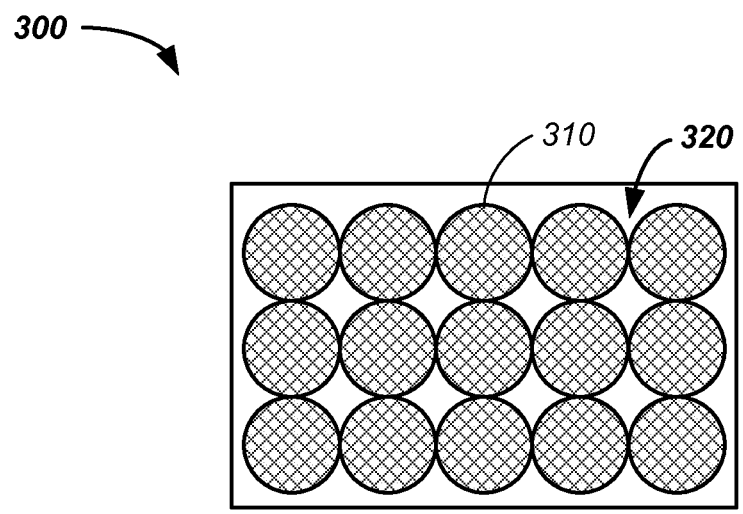
FIG. 3 illustrates schematically an aerosol foam.

Referring now to FIG. 3, aerosol foam 300 is depicted illustratively. The term "aerosol foam" is a product, which includes a liquid foamable composition and a propellant liquid, filled into a pressurized container that is equipped with a valve system and nozzle at the top of the container, and a dip tube that runs from the valve system to the bottom of the container. When the valve is open, the pressure on the liquid propellant is instantly reduced and it starts to evaporate forming a high-pressure gas layer at the top of the container. This high-pressure gas layer pushes the liquid product, as well as some of the liquid propellant, up the dip tube and out through the nozzle. When the liquids flow through the nozzle, the liquid propellant evaporates into gas and in the process forms propellant gas bubbles 310 in the liquid product 320 creating foam. Use of an aerosol foam results in a high velocity liquid emitting from the container. In the preferred formulations herein, the high velocity of the liquid emitting from the container provides excessive shear force that breaks apart the foam, which deposits the active agents in an unknown location. Additionally, activating a dispensing method from an aerosol container results in a highly imprecise volume of delivery; yielding a further unknown on the amount of active ingredient delivered to the desired area. Further, the density/viscosity combination of the formulations provided herein will not foam using an aerosol delivery method.

Non-Aerosol Non-Spray Foam

Figure 4:
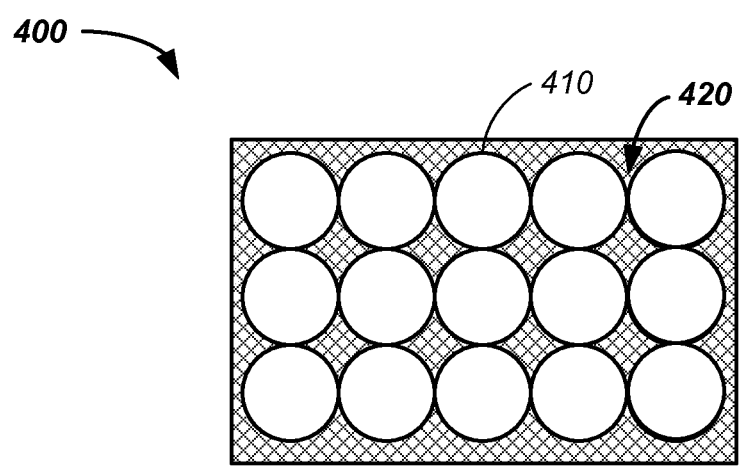
FIG. 4 illustrates schematically a non-aerosol, non-spray foam.

Referring now to FIG. 4, non-aerosol, non-spray foam 400 is depicted illustratively. The clause "non-aerosol, non-spray foam" is a product, which comprises a foamable liquid composition 420, which is filled into a non-pressurized container that is equipped with a mechanical pump, an air chamber, a mixing chamber, a foam forming screen mesh, and a dip tube that runs from the mechanical pump to the bottom of the container. When the mechanical pump is actuated, the foamable liquid composition 420 is forced up the dip tube into the mixing chamber where it is commingled with air from the air chamber, at a predetermined ratio to form foam. It is the actuation of the pump that pressurizes and causes the turbulent commingling of the air and the liquid foamable composition 420 to form air bubbles 410 in the foamable liquid composition 420 creating foam.

From the mixing chamber, the foam is then homogenized into fine uniform bubbles when it passes through the screen mesh before being dispensed out through the nozzle. Therefore, it is a non-propellant method of propelling the liquid product out of the container in the form of foam.

In summary, a major difference in the continuous state of the containers is that in an aerosol foam container the propellant fluid (typically compressed gas or liquefied gas) is pumped into the container under high pressure after the container is sealed and is maintained continuously in pressurized state, whereas in stark contrast in the container of the non-aerosol, non-spray foam, the air inside the container is constantly under atmospheric pressure. The high velocity of air/aerosol emitted from an aerosol delivery system is unsuitable for the below described formulation in terms of at least foam formation and foam stability.

As discussed, supra, the inventor discovered the surprising result that controlling the density of the hair loss formulation to less than one and very near one while additionally controlling the viscosity of the composition to less than the viscosity of water allows delivery of a temperature unstable foam, where foaming occurs at room temperature; the foam separates into a liquid phase and a foam phase within a short time period by raising the temperature of the foam to body temperature; the surface tension of the foam pins the liquid phase to the body while inverted due to the combined density and viscosity parameters; and slight compression at body temperature causes disruption of the foam to deliver the active agent to a desired location. Preferably, the viscosity of the foamable composition is within 0.01, 0.1, 0.5, 1, 2, or 5 percent of that of water, where water viscosity as a function of temperature is as in Table 1.

TABLE 1

Dynamic (Absolute) and Kinematic Viscosity of Water in SI Units

| Temperature (T) (° C.) | Dynamic Viscosity ($\mu$) (Pa s, N s/m$^2$) × 10$^{-3}$ | Kinematic Viscosity (v) (m$^2$/s) × 10$^{-6}$ |
|---|---|---|
| 20 | 1.002 | 1.004 |
| 30 | 0.798 | 0.801 |

Many laboratory experiments resulted in a surprising formulation yielding a stable foam for a short period of time at room temperature, a degraded stability of the foam on the palm of the hand forming a trapped liquid layer allowing transfer of a measured dosage to the scalp through a transition stage of an inverted palm, and immediate release of the active agent within the foam upon contact of the scalp by the hand, which yields both: (1) an accurate and precise measured dosage of the active ingredients and (2) an accurate and precise location of treatment that is simply not obtainable with a scattering aerosol delivered under pressure or a runny solution that is difficult to target to a precise area. The inventor further determined that small deviations from the precise formulation, as discussed infra, resulted in expected failure of foaming/delivery requirements, which indicates that those skilled in the art would have to undergo extensive research to determine the narrow formulation requirements achieved, just as Ph.D. level analytical chemists were required to develop the narrow formulation over an extended period of time. Representative data is provided herein to support the surprising results.

The precise formulation, detailed below, allows formation of a foam at room temperature, such as at 24±4° C., which degrades rapidly under slight compression and a small rise of temperature to surface body temperature of 32, 33, 34, 35, 36, and/or 37° C.

Referring now to Table 2, the precise formulation allows the foam to stay on the palm for a time period sufficient for delivery to the scalp in a precise and accurate area and with a precise and accurate dosage, which as described below is not possible with an aerosol or runny liquid. Particularly, in a final and/or very late stage of product formulation, the density of the formulation is adjusted to a narrow range of 0.89 to 1.0 g/mL. Indeed, formulations are preferably adjusted to a density of 0.995±0.005 g/mL to achieve all of the product specifications described herein. The density is adjusted through addition of an alcohol and/or ether thinning agent to the composition. Due to the required evaporative nature of elements of the formulation to result in rapid breakdown of the foam at body temperature, earlier adjustment of the density fails at a high rate as the formulation will continue to evaporate off key elements until packaged. Still referring to Table 2, the foam on the palm is observed to be stable for a time period sufficient for delivery of the foam from the palm of the hand to the targeted area of the scalp.

TABLE 2

Foam Stability on Palm

| Time (seconds) | Foam Percentage | Foam/Liquid Percentage on Palm |
|---|---|---|
| 0 | 100 | 100 |
| 20 | 75 | 100 |
| 60 | 50 | 100 |
| 120 | 25 | 100 |
| 180 | 10 | 100 |

Indeed, referring now to Table 3, the precise formulation forms a thin liquid layer on a palm of hand readying it for delivery, yet if the hand is tilted perpendicular to the floor or if the palm of the hand is inverted to face the floor, the foam clings to the palm trapping the liquid layer between the palm of the hand and the foam layer. Particularly, after delivering an accurate and precise dosage of the foam to an upright palm, via use of the pump/volume mechanism, the user has at least one minute to place the palm of their hand onto the desired treatment area even if the palm is inverted for the entire time. The precise density and viscosity of the formulation allows production of a foam that sticks to the inverted palm while trapping the forming liquid phase for rapid delivery.

TABLE 3

Foam Clinging to Inverted Palm

| Time (seconds) | Percentage Of Liquid/Foam Clinging to Inverted Palm |
|---|---|
| 0 | 100 |
| 30 | 100 |
| 60 | 100 |
| 90 | 90 |
| 90-120 | 20 |

Referring now to Table 4, once the foam is compressed between two body temperature, 34-37° C., surfaces, the foam immediately dissipates and delivers the active ingredients to the targeted location in and accurate and precise manner. For example, once the clinging foam and trapped liquid on the inverted palm of the hand touches the scalp, the vast majority of the foam is broken by the increased temperature, shear forces, and/or compression in two seconds with substantially complete delivery within ten seconds. The inventor notes that shampoo formulations completely fail to break apart in less than ten seconds, indeed, shampoo formulations are increasing in lather at that time period. Thus, modification of shampoo formulations for accurate and precise delivery of the pharmaceutical agents described herein requires extensive experimentation and modification, where theory fails due to the precise formulation requirements of the described composition.

TABLE 4

Foam Compressed Between Body Temperature Surfaces

| Time (seconds) | Liquid Percentage |
|---|---|
| 0 | 0 |
| 2 | 90 |

TABLE 4-continued

Foam Compressed Between Body Temperature Surfaces

| Time (seconds) | Liquid Percentage |
|---|---|
| 5 | 95 |
| 10 | 99 |

The surprising formulation yielding the properties described in Tables 1-3, comprises 0.1 to 10% minoxidil, preferably 3.0±1.5% minoxidil; 0.1 to 1.0% cetearyl glucoside, preferably 0.4±0.1% cetearyl glucoside; 0.001 to 0.4% 8-hydroxyquinoline sulfate, preferably 0.1±0.05% 8-hydroxyquinoline sulfate; 0.01 to 0.1% biotin, preferably 0.03±0.01% biotin, lactic acid, and/or water adjusted to a density of 0.995±0.005% g/mL with an alcohol and/or and an ether.

As described, supra, delivery of the active ingredient via an aerosol delivery method results in: (1) an imprecise dosage of the active ingredient as the user must control precisely the timing of release of the aerosol from the container and (2) an imprecise location of delivery of the active ingredient as the aerosol expands in a cone shape meaning that the user must accurately control distance of the canister above their head to a curved surface compensating for any air movement, such as from a heating/cooling system. The net result is that the active ingredient must be delivered with a higher dosage as much of the active ingredient goes to the atmosphere and to undesired regions of the body.

The inventor further notes that: (1) formulations with a density greater than 1 g/mL do not result in a density/viscosity combination that allows sustainability of the foam on an inverted palm; (2) delivery of the formulation in the above described embodiment is not possible with an aerosol as the shear forces of the aerosol exiting the container are sufficient to destroy stability of the foam with the formulated density/viscosity combination; and (3) formulations with higher viscosity require an aerosol for foam formation in the first place. For example, the high viscosity formulations of Tamarkin described in U.S. patent application no. 2008/0317679 A1 require a gas propellant aerosol delivery to generate the foam, as properly noted by Tamarkin, whereas the same gas propellant aerosol delivery would destroy foam formation in the surprising above described formulation. Any attempt to modify Tamarkin for delivery through a pump container, required for accurate dosage delivery, would be extensive requiring a complete redesign of the active ingredient, pH, solvent system to yield a precise viscosity and the noted density. The modification would require extensive experimentation where generic theory fails when forced to introduce particular chemical bonding agents of composition elements at precise pH levels, in particular solvents, having particular evaporation rates, and precise liquid trapping characteristics in terms of surface tension and clingability to skin. Further, modification of Tamarkin's formulation to the discovered formulation would destroy ability for delivery via aerosol as shear forces from the accelerant would destroy the foam prematurely.

Further, the surprising foam formulation is forced off of a target area with a stream of water, making is unsuitable for delivery and/or use under a stream of water from a shower. Hence, shampoo formulations are too stable. More particularly, shampoo formulations are designed to form a persistent foam or lather. As shampoo formulations yield a foam that persists, the surprising product formulation property of rapid dissipation of the foam at body temperature is not met. Indeed, shampoo formulations are designed to function at even higher shower temperatures, such as about 41-44° C. Hence, modification of a shampoo formulation destroys functionality of the shampoo formulation. Still further, compression of a shampoo formulation causes the bubbles to squeeze out of the compressed area, which would spread the active ingredient to undesirable areas as opposed to compression resulting in immediate collapse of the bubbles and delivery of the active agent to a desired region, as is provided in the preferred density/viscosity controlled formulation. Yet still further, shear forces of a shower stream would destroy and spread the foam formulation.

Additionally, shampoo formulations and/or aerosol delivery systems are unsuitable for delivery of the low concentrations of minoxidil described herein, such as less than four percent as the minoxidil in the prior art systems is spread to unwanted areas, such as running off of the scalp, to hair dense regions, to the atmosphere, and the like. Thus, the prior art systems are forced to deliver a higher concentration of minoxidil, such as greater than five percent and result in hair growth in undesired areas, such as already denser regions of hair, exacerbating the visual problem to be solved.

Non-Aerosol, Non-Spray Foam Pump and Container

In still yet another embodiment, a final product of a liquid formulation comprising the active ingredient minoxidil or a pharmaceutically acceptable salt thereof, that is packaged in a non-pressurized container 130, is dispensed using a non-aerosol, non-spray foam pump. The non-aerosol, non-spray foam pump provides for safe and simple dispensing of a measured dosage 262 of the foam that contains the liquid formulation comprising minoxidil or a salt thereof, that is readily applied 266 (breaks easily with shear) to the scalp. The non-aerosol, non-spray foam pump is calibrated to deliver an adequate volume of the foam.

An additional object herein disclosed is to provide the liquid formulation in a reusable 254 and non-pressurized container 130 that can be manufactured in a cylindrical 256 or non-cylindrical 258 shapes and that contains no propellant 252.

Therefore, the present embodiment does not employ the use of pressurized containers containing typical propellants, such as liquefied petroleum gases (mixture of propane, isobutene, and n-butane), chlorofluorocarbons (CFCs), and dimethyl ether, which are flammable, harmful, and toxic volatile organic compounds (VOCs). The present embodiment is safely transported, stored, and dispensed in reusable containers. Reusing products and the parts of products is extremely important for the safety and future of our planet.

Yet another aspect of the present embodiment relates to the orientation of the container when the product is being expelled; the foam can be easily and conveniently expelled in both horizontal (upright) and vertical positions.

Still another objective relates to the dispensing of a measured dosage of the liquid formulation; the container is calibrated to deliver an adequate volume of the foam that contains the liquid formulation comprising the active ingredient minoxidil or a pharmaceutically acceptable salt thereof.

Other objects are to provide a method for treating and/or preventing hair loss in humans, which is safe, simple, painless, cosmetic in the sense of being invisible, and easy to apply, where the methods comprise topically administering to the human scalp compositions.

Sunscreen

In still yet another embodiment, a protection agent is provided in the foamable minoxidil composition 110. The protection agent is delivered to a balding scalp in the foam and yields protection from the damaging effects of UV-A and/or UV-B irradiation, particularly solar radiation. Sunlight or ultraviolet radiation in the UV-B range has a wavelength of 290 nm to 320 nm and is known to be the primary cause of erythema, a reddening of the skin also known as sunburn. While, ultraviolet rays at a wavelength of 320 nm to 400 nm, known as UV-A radiation, produces tanning of the human epidermis. UV-A rays can also cause a loss in the elasticity of the skin and the appearance of wrinkles leading to a premature aging of the skin.

In this embodiment, the foamable minoxidil composition 110 or foamable liquid composition includes a sunscreen and/or a sun block agents, topically administered to the scalp in the cosmetically acceptable delivery vehicle of the non-aerosol, non-spray foam. The sunscreen and/or sun block 235 agents in the foamable minoxidil composition 110 or a minoxidil liquid formulation includes at least one of: an organic chemical compound that absorbs ultraviolet light, an inorganic particulate that reflects, scatters, and absorbs ultraviolet light, and an organic particulate that absorbs, reflects, and scatters ultraviolet light. Preferably, the sunscreen and/or sun block 235 agents yields a sun protection factor (SPF) in conjunction with the delivered foam of at least 1, 2, 3, 4, 5, 10, 15, 20, 30, or 40 to the scalp in the dosage of foam delivered for a unit dosage of minoxidil 210.

Foam Dispensing Device

Figure 5:
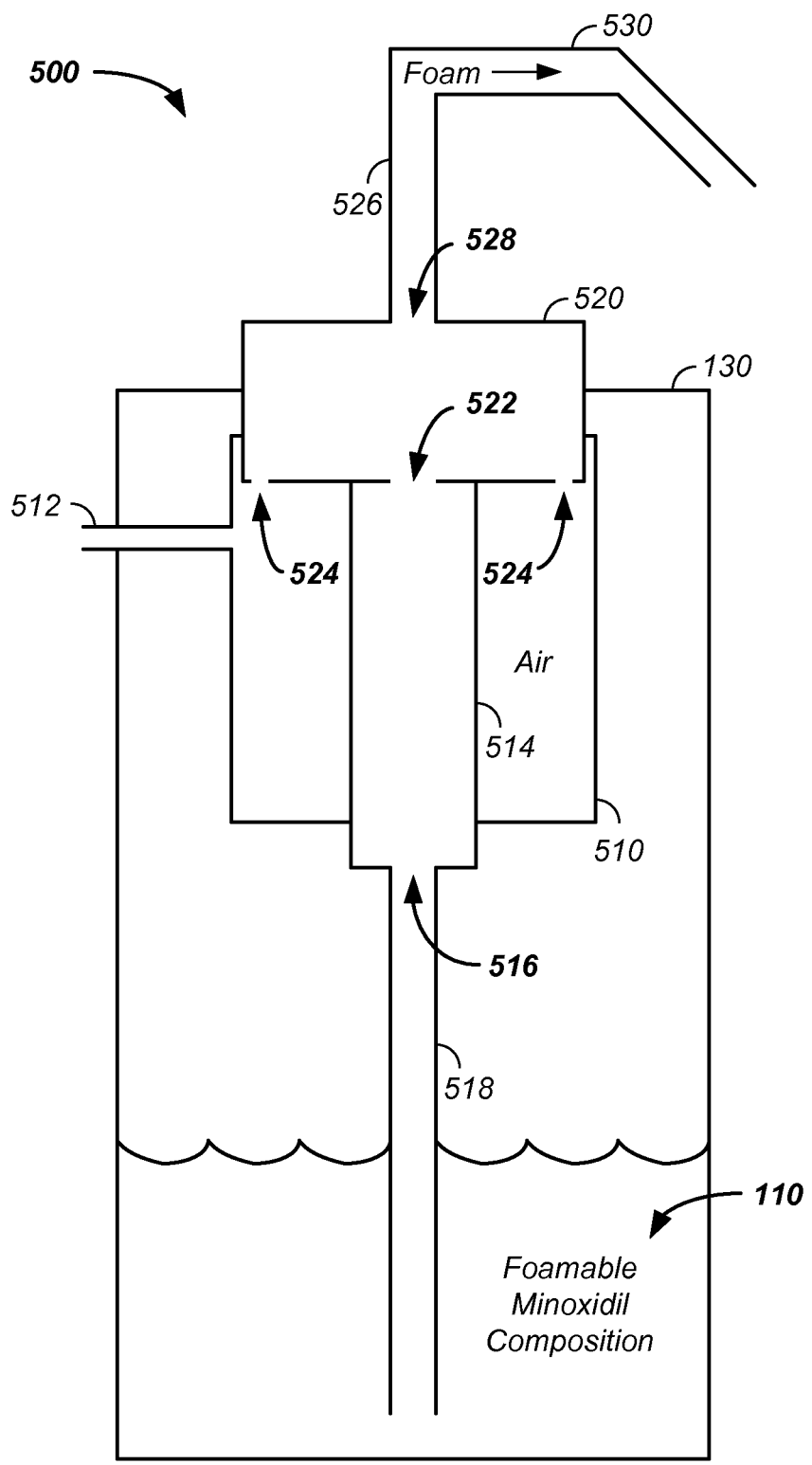
FIG. 5 illustrates a non-pressurized delivery container delivering a foam.

Referring now to FIG. 5, in yet another embodiment, a foam dispensing device 500 for dispensing the foamable minoxidil composition 110 as a foam includes one or more of: a non-pressurized container 130 for holding the foamable minoxidil composition 110, a foam generating unit 520, an air chamber 510, a liquid chamber 514, and an outflow channel 526 through which the foamed liquid product exits the foam dispenser through the nozzle 530. The liquid chamber 514 optionally includes a liquid inlet valve 516 and a liquid discharge valve 522. The air chamber 510 also optionally includes an air inlet valve 512 and an air discharge valve 524. The non-pressurized container 130 need not be cylindrical. The foam dispensing device 500, optionally further includes a dip tube 518, which draws the foamable minoxidil composition 110 from the bottom of the non-pressurized container 130 though the liquid chamber 514 and into the foam generating unit 520.

Operation of the foam dispensing device 500 occurs in the following manner. When downward pressure is applied against the nozzle 530, the air inlet valve 512 remains closed and the air in the air chamber 510 is compressed and forced through the air discharge valve 524 into the foam generating unit 520. Concurrently, the foamable minoxidil composition 110 in the liquid chamber 514 is forced through the liquid discharge valve 522 into the foam generating unit 520, where the turbulent commingling of the air and foamable minoxidil composition 110 creates foam. The resulting foam is expelled through the foam generating discharge valve 528 into the outflow channel 526 and out through an opening of the nozzle 530.

Once the downward pressure on the nozzle 530 is released, the resulting suction in the liquid chamber 514 forces open the liquid inlet valve 516, allowing the foamable minoxidil composition 110 to be suctioned through the dip tube 518 into the liquid chamber 514. The liquid discharge valve 522 remains closed during a return stroke. Concurrent with the release of the downward pressure on the nozzle 530, air is drawn into the air chamber 510 via the air inlet valve 512, bringing the pressure above the foamable minoxidil composition 110 in the non-pressurized container 130 back to atmospheric pressure.

Method of Use

Figure 6:
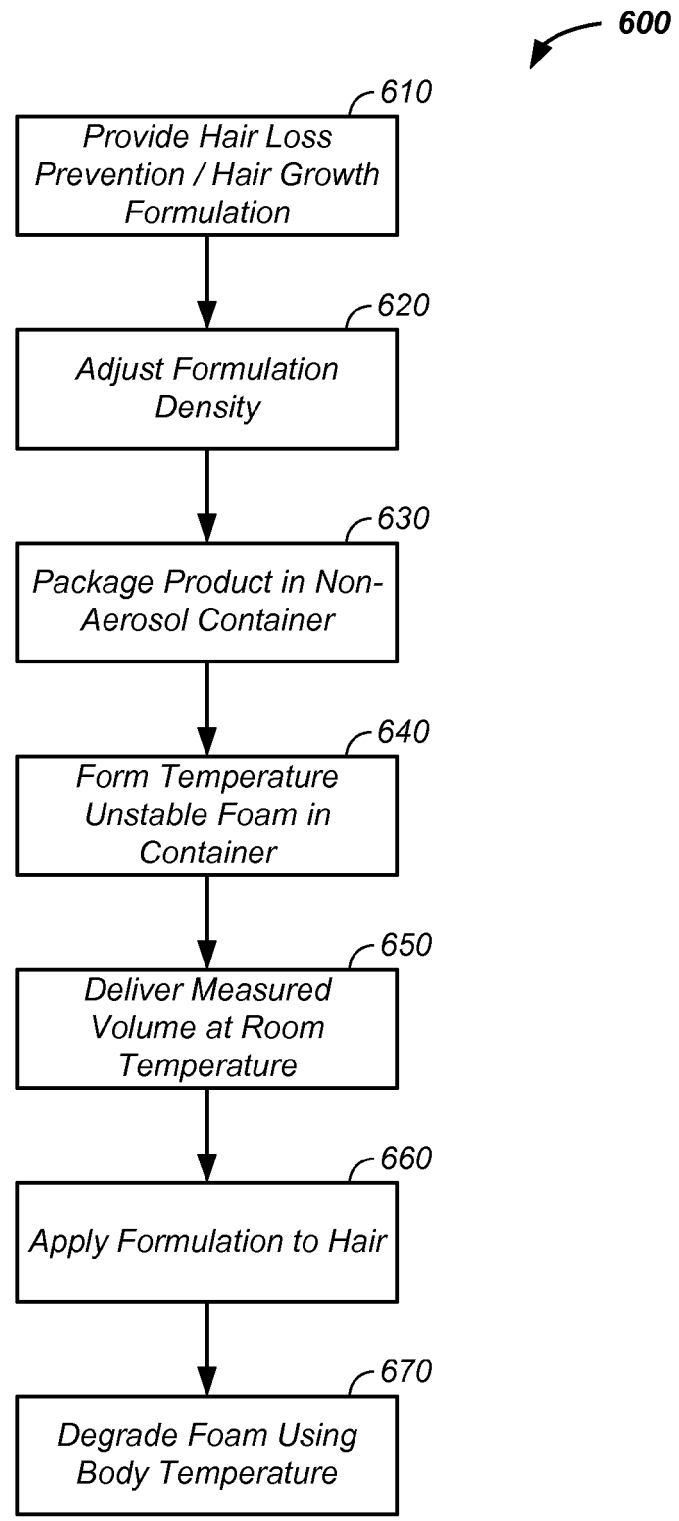
FIG. 6 illustrates a method of formulation and delivery of a temperature sensitive foam.

Referring now to FIG. 6, a method of formulation, delivery, and use of the formulation 600 is described. Steps for a preferred formulation/delivery/use of the density and viscosity controlled hair growth formulation include:
- substantially formulating 610 the hair loss prevention/hair growth formulation containing both minoxidil and at least one DHT inhibitor;
- at a late stage immediately prior to packaging, adjusting the formulation density 620 and/or viscosity using a thinning agent;
- packaging the composition 630 in a non-aerosol container, such as a pump volume dosage delivery foam generation container;
- using the pump and a mesh to form a temperature unstable foam 640 at room temperature;
- using the pump volume dosage delivery system to deliver a measured dosage 650 of the active ingredients at room temperature;
- applying the formulation to the scalp 660 through an inversion phase, such as with the low density foam sticking to a downward facing palm while trapping a forming liquid phase of the formulation; and
- rapidly degrading the foam 670 when placed between two body temperature surfaces.

Although the invention has been described herein with reference to certain preferred embodiments, one skilled in the art will readily appreciate that other applications may be substituted for those set forth herein without departing from the spirit and scope of the present invention. Accordingly, the invention should only be limited by the Claims included below.

The invention claimed is:

1. A method for delivering a liquid as a foam for the treatment of hair loss of a human user, said method comprising the steps of:
   providing a liquid formulation comprising:
      a first hair growth constituent comprising a minoxidil concentration of one-tenth to four percent by weight
      a first hair loss blocker comprising a cetearyl glucoside concentration of one-tenth to one percent by weight;
      a second hair loss blocker comprising a 8-hydroxyquinoline sulfate concentration of 0.001 to 0.4 percent by weight,
      lactic acid; water; and at least one of an alcohol and an ether;
   adjusting said liquid formulation to comprise a first formulation specification range of a formulation viscosity within one-half of one percent of that of water viscosity at standard temperature and pressure, wherein said formulation viscosity is less than said water viscosity;
   after preparation of said liquid formulation, adjusting said liquid formulation to a second formulation specification range of a density of 0.995±0.005% g/mL to form a foamable formulation;
   packaging said foamable formulation in a non-aerosol delivery container comprising a calibrated pump delivery volume, said step of packaging occurring prior to evaporation of at least one of said alcohol and said ether of said liquid formulation moving said foamable formulation out of at least one of said first formulation specification range and said second formulation specification range;
   pumping said non-aerosol delivery container to force a measured pump volume of said foamable formulation through a screen to form a foam at room temperature, said formulation viscosity yielding a substantially uniform and self-adhering froth under pressures resultant from manual actuation of said measured pump volume while failing to form a uniform froth under shear forces from an aerosol delivery system, said step of pumping delivering said foam to a palm of the user;

said foam forming a liquid layer trapped between said foam and the palm, said liquid layer comprising less than twenty percent of the volume of said foam;

inverting said palm to deliver the foam and the liquid layer to a targeted scalp location, said liquid layer substantially trapped between the inverted palm and the foam until at least one of: delivery to said scalp and at least sixty seconds; and upon substantial contact of the inverted palm and the scalp, the foam substantially dissipating within five seconds at surface body temperature of 33-37° C. to substantially deliver said minoxidil to a targeted area without any of: running off of the scalp and being dissipated by air currents.

2. The method of claim 1, wherein said minoxidil concentration comprises at least one of:

3.0±1.5% minoxidil;

3.0±1.5% of a pharmaceutical salt of minoxidil; and 3.0±1.5% of a combination of said minoxidil and said pharmaceutical salt of minoxidil;

wherein said cetearyl glucoside concentration comprises 0.4±0.1 percent cetearyl glucoside;

wherein said 8-hydroxyquinoline sulfate concentration comprises 0.1±0.05 percent 8-hydroxyquinoline sulfate; and wherein said biotin concentration comprises 0.03±0.01 percent biotin.

3. The method of claim 2, said step of pumping further comprising:

commingling, without use of a propellant, air and the foamable composition in a non-pressurized container to form said foam within a foam generating unit of said non-pressurized container, said container configured to dispense a measured dosage of said foam state of said foamable composition from said non-pressurized container.

4. The method of claim 2, said non-aerosol delivery container further comprising:

an air chamber within said non-pressurized container, said air chamber configured to hold non-pressurized air;

a first piston configured to slideably move within said air chamber;

a second piston configured to slideably move within a liquid chamber; and a screen mesh positioned in a foam generating unit prior to an outflow channel of said non-pressurized container, said first piston and said second piston configured to move concurrently to:

move the air into said foam generating unit; and force said foamable composition from said liquid chamber into said foam generating unit.

5. The method of claim 4, said foamable composition further comprising:

a lower alcohol comprising one to four carbon atoms per molecule, said lower alcohol comprising at least one of:

methanol;

ethanol;

propanol; and isopropyl alcohol.

6. The method of claim 5, said foamable composition further comprising:

an ultraviolet radiation protective agent comprising an inorganic particulate that reflects, scatters, and absorbs ultraviolet light.

7. The method of claim 6, said foamable composition further comprising:

oleth-20.

8. The method of claim 7, further comprising the step of:

homogenizing the foam in said foam generating unit by passing the foam through a screen mesh into an outflow channel of said non-pressurized container.

9. The method of claim 3, further comprising the step of:

applying a human pump force to a nozzle of said non-pressurized container, said applied human force used in said step of commingling.

* * * * *